United States Patent
Eckerdal

(10) Patent No.: US 9,283,395 B2
(45) Date of Patent: Mar. 15, 2016

(54) CARDIAC STIMULATING DEVICE

(71) Applicant: ST. JUDE MEDICAL AB, Jarfalla (SE)

(72) Inventor: Johan Eckerdal, Knivsta (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 229 days.

(21) Appl. No.: 14/190,554

(22) Filed: Feb. 26, 2014

(65) Prior Publication Data
US 2014/0180352 A1    Jun. 26, 2014

Related U.S. Application Data

(62) Division of application No. 13/509,556, filed as application No. PCT/EP2009/066594 on Dec. 8, 2009, now Pat. No. 8,700,153.

(51) Int. Cl.
| | |
|---|---|
| A61N 1/00 | (2006.01) |
| A61N 1/372 | (2006.01) |
| A61N 1/362 | (2006.01) |
| A61N 1/37 | (2006.01) |
| A61N 1/368 | (2006.01) |

(52) U.S. Cl.
CPC .......... *A61N 1/37276* (2013.01); *A61N 1/3622* (2013.01); *A61N 1/371* (2013.01); *A61N 1/3688* (2013.01)

(58) Field of Classification Search
CPC ... A61N 1/3622; A61N 1/3688; A61N 1/371; A61N 1/37276
USPC .............................................. 607/5, 9, 18, 25
See application file for complete search history.

(56) References Cited

U.S. PATENT DOCUMENTS

| | | | |
|---|---|---|---|
| 5,928,271 A | 7/1999 | Hess et al. | |
| 6,473,649 B1 | 10/2002 | Gryzwa et al. | |
| 6,952,609 B1 * | 10/2005 | Lindgren | A61N 1/368 607/15 |

FOREIGN PATENT DOCUMENTS

EP    0770408 B1    3/2004

OTHER PUBLICATIONS

Restriction Requirement, mailed Mar. 29, 2013: Parent U.S. Appl. No. 13/509,556.
NonFinal Office Action, mailed Jul. 18, 2013: Parent U.S. Appl. No. 13/509,556.
Notice of Allowance, mailed Dec. 11, 2013: Parent U.S. Appl. No. 13/509,556.

* cited by examiner

*Primary Examiner* — Niketa Patel
*Assistant Examiner* — Lindsey G Hankins

(57) ABSTRACT

An implantable medical device, IMD, comprises atrial and ventricular sensing units for sensing atrial or ventricular electric events. The IMD also comprises atrial and ventricular pulse generators for generating atrial or ventricular pacing pulses. A controller controls the operation of the IMD (100) according to a first mode, in which the ventricular pulse generator is prevented from generating a back-up pulse if an evoked response detector fails to detect evoked response to a delivered ventricular pacing pulse, and a second mode, in which the ventricular pulse generator is controlled to generate a back-up pulse if no evoked response is detected following delivery of a ventricular stimulating pulse. The controller switches operation from the first mode to the second mode based on the evoked response detector failing to detect an evoked response to a delivered ventricular pacing pulse.

9 Claims, 5 Drawing Sheets

CARDIAC STIMULATING DEVICE

CROSS REFERENCE TO RELATED APPLICATIONS

This application is a division of U.S. patent application Ser. No. 13/509,556, filed May 11, 2012, which is a 371 of International Application No. PCT/EP2009/066594, filed Dec. 8, 2009.

TECHNICAL FIELD

The present invention generally relates to implantable cardiac stimulating devices, and in particular to dual chamber implantable cardiac stimulating devices.

BACKGROUND

Implantable cardiac stimulating devices capable of emitting back-up pulses to a heart ventricle when no evoked to a previously applied ventricular pacing pulse are known in the art, see U.S. Pat. No. 5,476,487.

This type of cardiac stimulating devices is generally denoted as autocapture pacemakers in the art. The autocapture pacemakers operate by sensing whether a response occurs in the ventricle shortly after a ventricular pacing pulse has been delivered, such as 5-20 ms after delivery. The sensing may, for instance, take place during 40-60 ms. If a response is sensed during this time interval then no back-up pulse is emitted. However, if no evoked response is sensed, the pacemaker emits a back-up pulse. The back-up pulse is usually emitted with increased output energy or power in order to secure capture of the heart. For example, a normal value for a ventricular pacing pulse could be an amplitude of about 1.5 V, whereas the back-up pulse can be emitted with an amplitude of about 4.5 V.

Sometimes a back-up pulse can be delivered to the ventricle during a phase of the heart cycle when a stimulating pulse is not wanted. Such unwanted pulses may be initiated, for instance, after the occurrence of a premature ventricular contraction (PVC). If such a PVC occurs more or less simultaneously with an atrial event, the PVC may be undersensed due to ventricular blanking after atrial stimulation. In such a case, a ventricular pacing pulse may be delivered in the refractory period after the PVC, during which the heart will not respond to the ventricular stimulation. No evoked response will consequently be detected and a back-up pulse is delivered. In an unfortunate case, the back-up pulse can be timed with the vulnerable period after the PVC, typically coincident with a part of the T-wave, during which a delivered stimulation pulse may induce repetitive rhythms, such as for example tachycardia or ventricular fibrillation (VF).

U.S. Pat. No. 6,952,609 discloses an implantable cardiac stimulating device capable of combating these problems of increased risk of unintentionally triggering tachycardia or VF due to unfortunate timing of back-up pulses. The implantable cardiac stimulating device has a control unit for controlling an atrial pulse generator dependent on an atrial sensing unit, in a first manner wherein no stimulating pulse is delivered to the atrium and in a second manner wherein stimulating pulses are delivered to the atrium. The control unit additionally prevents delivery of back-up pulses to the ventricle during a number of heart cycles when the control unit changes from the first manner of operation to the second manner of operation.

SUMMARY

There is still a need for improvements relating to reducing the risk of unintentional triggering of tachycardia or VF due to delivery of back-up pulses in a vulnerable period.

It is an objective to provide an implantable cardiac stimulating device with reduced risk of triggering tachycardia and ventricular fibrillation.

It is a particular objective to provide a multi-mode implantable cardiac stimulating device suitable for handling PVCs and undersensed ventricular events.

These and other objectives are met by embodiments as defined by the accompanying patent claims.

Briefly, an implantable cardiac stimulating device comprises a lead connector electrically connectable to an atrial lead and a ventricular lead. The device comprises an atrial pulse generator for generating atrial stimulating pulses and a ventricular pulse generator for generating ventricular stimulating pulses. An atrial sensing unit is implemented to sense any electric events in an atrium of a heart and a ventricular sensing unit correspondingly is configured to sense any electric events in a ventricle of the heart. The device also comprises an evoked response detector implemented to detect capture or evoked response of the ventricle to a ventricular stimulating pulse generated by the pulse generator.

A controller is connected to the pulse generators and the sensing units and controls the operation of the ventricular pulse generator according to a first mode or a second mode. In the first mode, the controller prevents the ventricular pulse generator from generating a back-up pulse if the evoked response detector does not detect an evoked response to a delivered ventricular stimulating pulse. However, in the second mode, the controller controls the ventricular pulse generator to generate a back-up pulse if no evoked response is detected by the evoked response detector in response to a delivered ventricular stimulating pulse.

The device is normally operated according to the first mode and the controller switches operation to the second mode based on the evoked response detector failing to detect an evoked response to a delivered ventricular stimulating pulse.

By preventing the delivery of a back-up pulse the first time ventricular capture does not occur in response to a ventricular stimulating pulse, the IMD significantly reduces the risk of delivering back-up pulses during the vulnerable period of an undersensed PVC or intrinsic ventricular event. In clear contrast, a back-up pulse is delivered first the second time ventricular capture fails during two consecutive heart cycles. The risk of having two PVCs that both occur during the ventricular blanking period in two consecutive heart cycles is next to neglectable. As a consequence, the IMD can therefore safely deliver the back-up pulse in this second heart cycle if no evoked response is detected.

Another aspect relates to a cardiac stimulating method comprising starting a first atrial escape interval (AEI) and delivering an atrial stimulating pulse to the atrium if no electric event of the atrium is detected before expiry of the first AEI. A first atrioventricular interval (AVI) is started based on detection of the electric event of the atrium or based on delivery of the atrial stimulating pulse. A ventricular stimulating pulse is delivered to the ventricle following expiry of the first AVI if no electric event of the ventricle has been detected at the expiry of the first AVI. An evoked response of the ventricle to the ventricular stimulating pulse is monitored and if no such evoked response is detected a second AEI equal to or shorter than the first AEI is started. An atrial stimulating pulse is delivered to the atrium if no electric event of the atrium is detected before the expiry of the second AEI. A second AVI, equal to or shorter than the first AVI, is started based on detection of the electric event of the atrium or based on delivery of the atrial stimulating pulse. A ventricular stimulating pulse is delivered to the ventricle following expiry of the second AVI if no electric event of the ventricle is detected before the expiry of the second AVI. An evoked response of the ventricle to the ventricular stimulating pulse is monitored and if no such evoked response is detected a back-up pulse is delivered to the ventricle and the first AEI is started.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present invention generally relates to implantable medical devices (IMDs) and methods of operating such devices, and in particular to dual chamber implantable cardiac stimulating devices capable of operating in multiple operation modes.

The IMD of the invention is operable according to at least two different modes and is due to this multi-mode operation designed to be particularly suitable for patients running a risk of having PVCs. The multi-mode IMD is in particular configured to prevent or at least significantly reduce the risk of unintentionally inducing repetitive rhythms, such as tachycardia or ventricular fibrillation of the paced heart by delivering back-up pulses in the vulnerable period after previous undersensed PVC.

Figure 1:
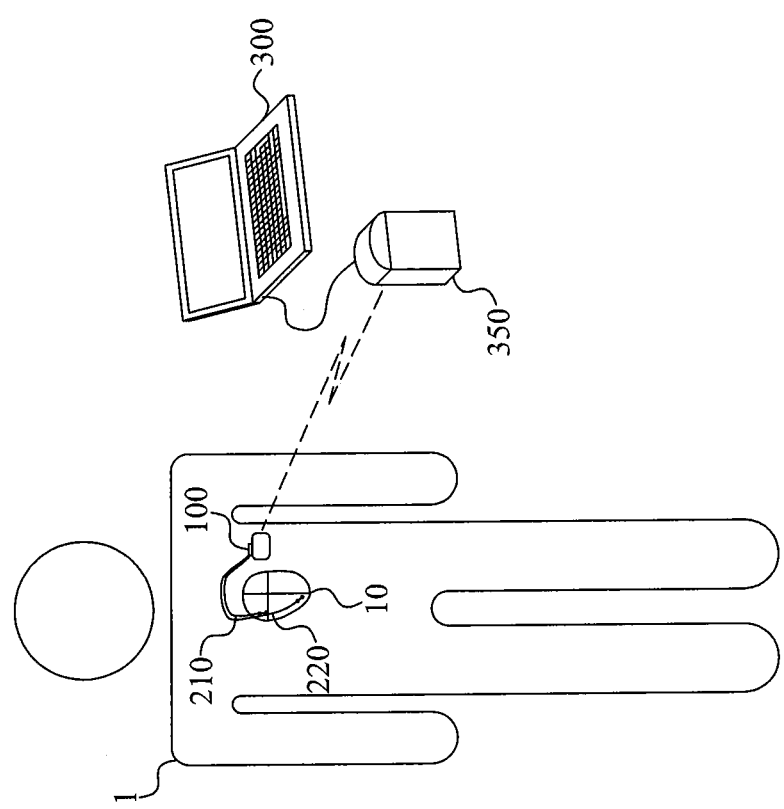
FIG. 1 is a schematic overview of a subject equipped with an implantable cardiac stimulating device according to an embodiment.

FIG. 1 is a schematic overview of a human patient 1 having an IMD 100. In the figure, the IMD 100 is illustrated as a device that monitors and/or provides therapy to the heart 10 of the patient 1, such as a pacemaker, cardiac defibrillator or cardioverter capable of delivering stimulating cardiac pacing therapy. The IMD 100 is, in operation, connected to two or more, two in the figure, cardiac leads 210, 220 inserted into or provided in connection with heart chambers, preferably in the form of at least one atrial lead 210 and at least one ventricular lead 220.

The figure also illustrates an external programmer or clinician's workstation 300 that can communicate with the IMD 100, optionally through a communication unit 350 that operates similar to a base station on behalf of the programmer 300. As is well known in the art, such a programmer 300 can be employed for transmitting IMD programming commands, causing a reprogramming of different operation parameters and modes of the IMD 100. Furthermore, the IMD 100 can upload diagnostic data descriptive of different medical parameters or device operation parameters collected by the IMD 100 to the programmer 300.

Figure 2:
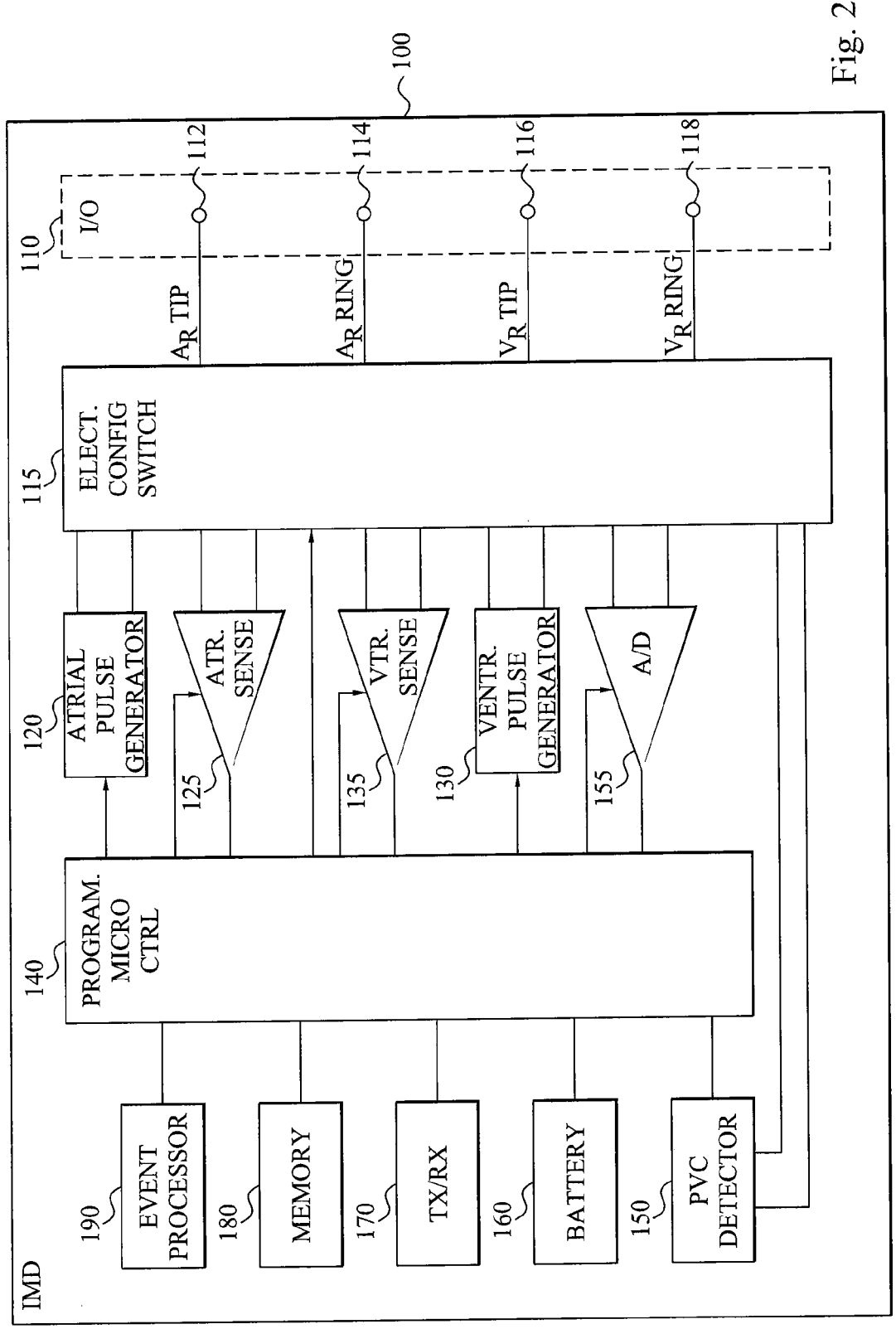
FIG. 2 is block diagram of an embodiment of an implantable cardiac stimulating device.

FIG. 2 illustrates an embodiment of an IMD 100 suitable for delivering cardiac therapy to a heart of a subject. The figure is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs as long as the IMD is capable of dual chamber operation with both atrial and ventricular sensing and pulsing. Accordingly, the person skilled in the art can readily duplicate, eliminate, or disable the appropriate circuitry in any desired combination to provide an IMD capable of treating the appropriate heart chamber(s) with pacing stimulation and optionally also cardioversion and/or defibrillation.

Figure 4:
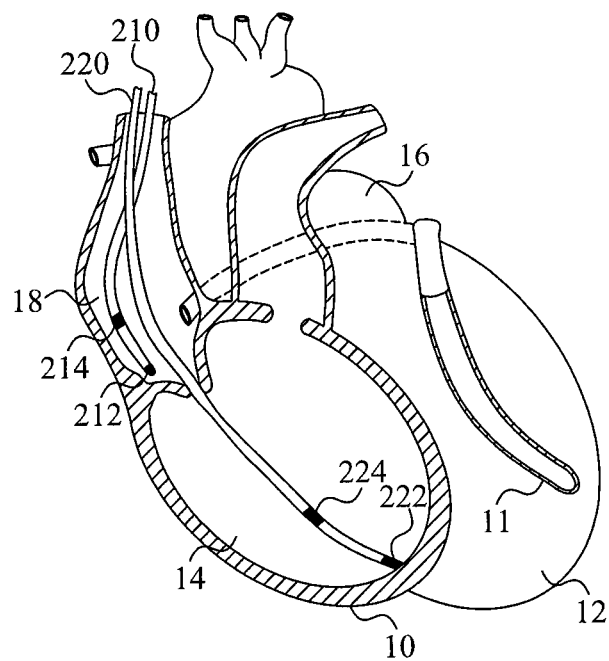
FIG. 4 illustrates a set of cardiac leads connectable to an implantable cardiac stimulating device according to an embodiment.
Figure 5:
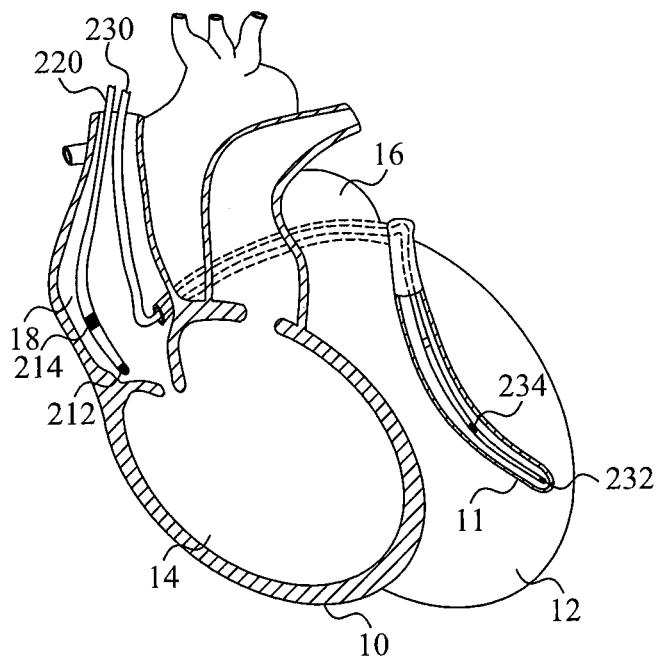
FIG. 5 illustrates another set of cardiac leads connectable to an implantable cardiac stimulating device according to an embodiment.

The IMD 100 comprises a housing, often denoted as can or case in the art. The housing can act as return electrode for unipolar leads, which is well known in the art. The IMD 100 also comprises a lead connector or input/output (I/O) 110 having, in this embodiment, a plurality of terminals 112-118. With reference to FIGS. 2, 4 and 5. The lead connector 110 is configured to be, during operation in the subject body, electrically connectable to at least one atrial lead 210 and at least one ventricular lead 220, 230. The lead connector 110 consequently comprises terminals 112, 114 that are electrically connected to matching electrode terminals of an atrial lead 210 when the atrial lead 210 is introduced in the lead connector 110. For instance, one of these terminals 112 can be designed to be connected to a right atrial tip terminal of the atrial lead 210, which in turn is electrically connected through a conductor running along the lead body to a tip electrode 212 present at the distal end of the atrial lead 210 in the right atrium 18 of the heart 10. A corresponding terminal 114 is then connected to a right atrial ring terminal of the atrial lead 210 that is electrically connected by another conductor in the lead body to a ring electrode 214 present in connection with the distal part of the atrial lead 210, though generally distanced somewhat towards the proximal lead end as compared to the tip electrode 212.

In an alternative implementation, the IMD 100 is not connectable to a right atrial lead 210 but instead to a left atrial lead configured for implantation in the left atrium 16. A further possibility is to have an IMD 100 with a lead connector 110 having sufficient terminals to allow the IMD 100 to be electrically connectable to both a right atrial lead 210 and a left atrial lead.

In order to support right chamber sensing and pacing, the lead connector 110 further comprises a right ventricular tip terminal 116 and a right ventricular ring terminal 118, which are adapted for connection to a right ventricular tip electrode 222 and a right ventricular ring electrode 224 of a right ventricular lead 220 implantable in the right atrium 14.

In an alternative embodiment, the lead connector 110 is connectable to a left ventricular lead 230 instead of a right ventricular lead 220. A left ventricular lead 230 is typically implanted in the coronary sinus 11 for safety reasons although implantation inside the left ventricle 12 has been proposed in the art. In the following, "left ventricular lead" 230 is used to describe a cardiac lead designed to provide sensing and pacing functions to the left ventricle 12 regardless of its particular implantation site, i.e. inside the left ventricle 12 or in the coronary sinus 11. The left ventricular lead 230 preferably also comprises a tip electrode 232 and a ring electrode 234 as the right ventricular lead 220 of FIG. 4.

Also a combination of a right ventricular lead 220 and a left ventricular lead 230 can be used with the IMD 100 with a lead connector 110 then having the appropriate number of terminals.

The cardiac leads 210, 220, 230 connectable to the IMD 100 can comprise one or more electrodes 212, 214, 222, 224, 232, 234 to be placed in or in connection with the relevant heart chamber 12, 14, 16, 18 following implantation. In the figure, this has non-limitedly been exemplified by two electrodes 212, 214, 222, 224, 232, 234 per cardiac lead 210, 220, 230. However, also so-called multi-electrode leads could be connectable to the lead connector 110, where such a multi-electrode lead has three or more electrodes, generally in the form of one tip electrode and then multiple, i.e. at least two, spatially separated ring electrodes or at least three ring electrodes with no tip electrode.

The IMD 100 as illustrated in FIG. 2 comprises an atrial pulse generator 120 and a ventricular pulse generator 130 that generate pacing pulses for delivery by the atrial lead(s) and the ventricular lead(s) preferably through an electrode configuration switch 115.

It is understood that in order to provide stimulation therapy in different heart chambers, the atrial and ventricular pulse generators 120, 130 may include dedicated, independent pulse generators, multiplexed pulse generators, or shared pulse generators. The pulse generators 120, 130 are controlled by a controller 140 via appropriate control signals, respectively, to trigger or inhibit the stimulation pulses.

The IMD 100 also comprises a controller 140, preferably in the form of a programmable microcontroller 140 that controls the operation of the IMD 100. The controller 140 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 140 is configured to process or monitor input signal as controlled by a program code stored in a designated memory block. The type of controller 140 is not critical to the described implementations. In clear contrast, any suitable controller may be used that carries out the functions described herein. The use of microprocessor-based control circuits for performing timing and data analysis functions are well known in the art.

The controller 140 further controls the timing of the stimulation pulses, such as pacing rate, atrioventricular interval (AVI), atrial escape interval (AEI) etc. as well as to keep track of the timing of refractory periods, blanking periods, noise detection windows, evoked response windows, alert intervals, marker channel timing, etc. In a particular embodiment the controller 140 is preferably employed by the IMD 100 for determining AEI and AVI according different operation modes, which is further described herein.

A preferred electronic configuration switch 115 includes a plurality of switches for connecting the desired terminals 112-118 to the appropriate I/O circuits, thereby providing complete electrode programmability. Accordingly, the electronic configuration switch 115, in response to a control signal from the controller 140, determines the polarity of the stimulation pulses (e.g., unipolar, bipolar, combipolar, etc.) by selectively closing the appropriate combination of switches (not shown) as is known in the art.

An atrial sensing circuit or detector 125 and a ventricular sensing circuit or detector 135 are also selectively coupled to the atrial lead(s) and the ventricular lead(s) through the switch 115 for detecting the presence of cardiac activity in the heart chambers. Accordingly, the atrial and ventricular sensing circuits 125, 135 may include dedicated sense amplifiers, multiplexed amplifiers, or shared amplifiers. The switch 115 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture as is further mentioned herein.

Each sensing circuit 125, 135 preferably employs one or more low power, precision amplifiers with programmable gain and/or automatic gain control, bandpass filtering, and a threshold detection circuit, as known in the art, to selectively sense the cardiac signal of interest.

The outputs of the atrial and ventricular sensing circuits 125, 135 are connected to the controller 140, which, in turn, is able to trigger or inhibit the atrial and ventricular pulse generators 120, 130, respectively, in a demand fashion in response to the absence or presence of cardiac activity in the appropriate chambers of the heart.

Furthermore, the controller 140 is also capable of analyzing information output from the sensing circuits 125, 135 and/or a data acquisition system 155 to determine or detect whether and to what degree tissue capture has occurred and to program a pulse, or pulse sequence, in response to such determinations. The sensing circuits 125, 135, in turn, receive control signals over signal lines from the controller 140 for purposes of controlling the gain, threshold, polarization charge removal circuitry, and the timing of any blocking circuitry coupled to the inputs of the sensing circuits 125, 135 as is known in the art.

Cardiac signals are also applied to inputs of an optional analog-to-digital (ND) data acquisition system 155. The data acquisition system 155 is configured to acquire intracardiac electrogram signals, convert the raw analog data into a digital signal, and store the digital signals for later processing and/or transmission to the programmer by a transceiver 170. The data acquisition system 155 is coupled to the atrial lead and/or the ventricular lead through the switch 115 to sample cardiac signals across any pair of desired electrodes.

The controller 140 is further coupled to a memory 180 by a suitable data/address bus, wherein the programmable operating parameters used by the controller 140 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, and time interval between pacing pulse of an applied pacing pulse sequence.

Advantageously, the operating parameters of the IMD 100 may be non-invasively programmed into the memory 180 through a transceiver 170 in communication via a communication link with the previously described communication unit of the programmer. The controller 140 activates the transceiver 170 with a control signal. The transceiver 170 can alternatively be implemented as a dedicated receiver and a dedicated transmitter connected to separate antennas or a common antenna, preferably a radio frequency (RF) antenna.

The IMD 100 additionally includes a battery 160 that provides operating power to all of the circuits shown in FIG. 2.

Figure 3:
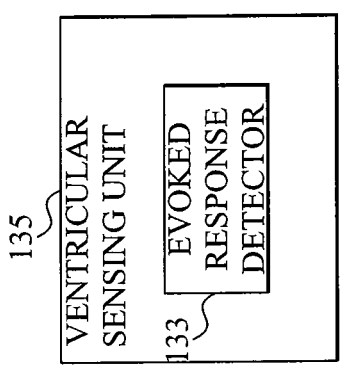
FIG. 3 is a block diagram of an embodiment of the ventricular sensing unit in the implantable cardiac stimulating device of FIG. 2.

The ventricular sensing unit 135 preferably comprises an evoked response detector 133, which is illustrated in the schematic block diagram of FIG. 3. The evoked response detector 133 is in particular implemented in the IMD for detecting an evoked response of a heart ventricle in response to a ventricular stimulating pulse previously generated by the ventricular pulse generator and delivered to the ventricle by the connected ventricular lead. In an embodiment, the evoked response detector 133 generates an evoked response detection signal upon detection of an evoked response of the monitored ventricle(s). This detection signal is forwarded to the controller 140 and is employed for the IMD control as is disclosed below. In FIG. 3, the evoked response detector 133 has been illustrated as forming part of the ventricular sensing unit 135. An alternative embodiment has the evoked response detector 133 implemented elsewhere in the IMD preferably connected to the controller and the switch. In a further alternative embodiment, the evoked response detecting function of the evoked response detector 133 is performed by the ventricular sensing unit 135, which then has dual functions.

According to the invention, the controller 140 in the IMD 100 is configured to control the operation of ventricular pulse generator 130 and preferably also the atrial pulse generator 120 according to at least a first mode and a second mode. Additionally, the controller 140 is configured to switch operation from the first mode to the second mode based on the detection result of the evoked response detector 133.

In more detail, the controller 140 switches operation from the first mode to the second mode if the evoked response detector 133 fails to detect an evoked response to a delivered ventricular stimulating pulse.

Thus, following generation of a ventricular stimulating pulse by the ventricular pulse generator 130 and delivery of the stimulating pulse through the switch 115 and the ventricular lead, the controller 140 controls the evoked response detector 133 to start sensing whether a response to the stimulating pulse occurs in the ventricle. For instance, the controller 140 can control the evoked response detector 133 to start this sensing following a blanking period of about 5-20 ms after the stimulating pulse delivery. The evoked response detector 133 performs the sensing, for example, during a time window of 40-60 ms or some other defined evoked response time window, which may optionally be controlled by the controller 140. If the evoked response detector 133 detects an evoked response in this time window, it generates and forwards the evoked response detection signal to the controller 140. The controller 140 thereby does not trigger any mode switch but continuous operating in the first mode, which is preferably the default operation mode of the IMD 100.

However, following expiry of the evoked response time interval and if the evoked response detector 133 has not detected any evoked response and forwarded an evoked response detection signal to the controller 140, the controller 140 triggers a mode switch from the current first mode to the second mode.

When operating in the first mode, the controller 140 is configured to prevent the ventricular pulse generator 130 from generating a back-up pulse if the evoked response detector does not detect an evoked response to a delivered ventricular stimulating pulse. Thus, in clear contrast to the prior art Autocapture technique when no evoked response is detected, no back-up pulse is delivered but instead a switch in operation mode is performed by the IMD 100.

However, when operating in the second mode the controller 140 is configured to control the ventricular pulse generator 130 to generate a back-up pulse that is delivered to the ventricle by the ventricular lead if the evoked response detector does not detect an evoked response to a delivered ventricular stimulating pulse. Thus, a back-up pulse is generated by the IMD 100 in the second mode but not in the first mode. This mode-specific back-up pulse generation reduces the risk of delivering back-up pulses in the vulnerable period of undersensed PVCs or indeed undersensed intrinsic ventricular events, such as due to inappropriate IMD sense settings.

Figure 6:
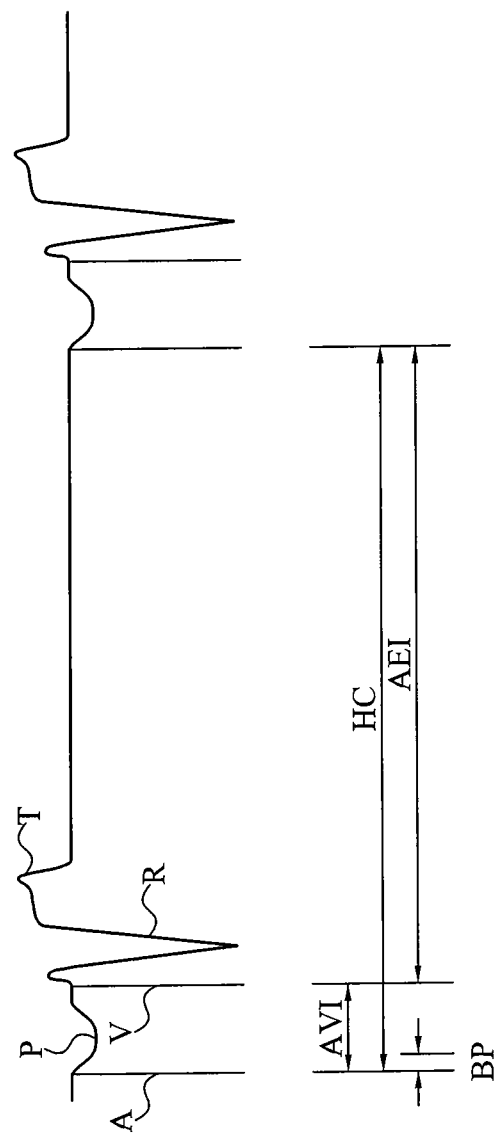
FIG. 6 is a timing/waveform diagram illustrating cardiac pacemaker events in conventional dual chamber implantable cardiac stimulating devices.
Figure 7:
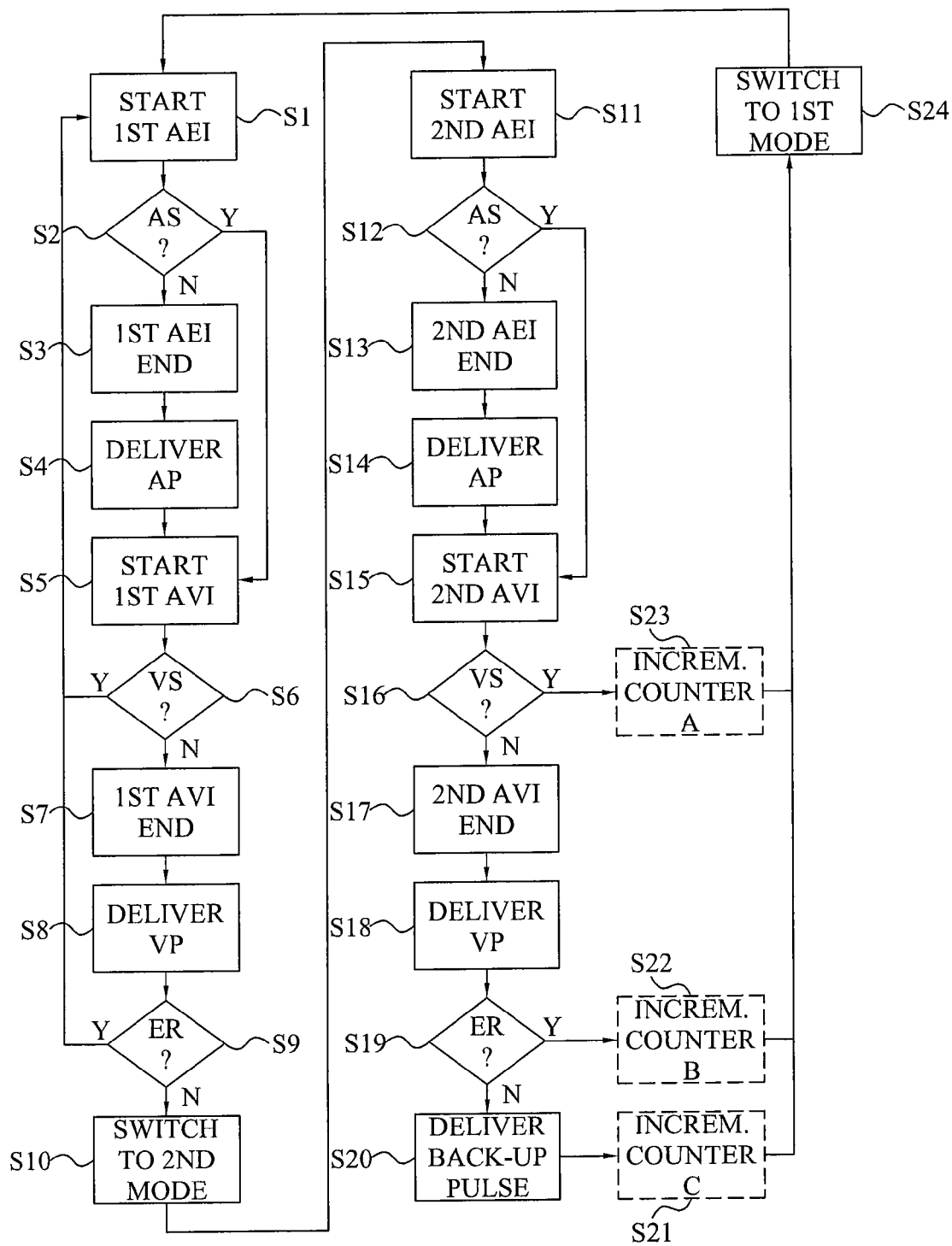
FIG. 7 is flow diagram illustrating a cardiac stimulating method.

The operation of the IMD in the different modes will now be described in more detail with reference to FIGS. 6 and 7. The IMD is preferably configured to start operation in the first mode, which therefore can be regarded as default or standard mode, with the second mode as an auxiliary mode that is triggered under specific conditions. The cardiac stimulating method starts in step S1, where a first AEI is set to indicate a new cardiac or heart cycle (HC). The AEI indicates the atrial escape interval and is a time interval that starts with an atrial or a ventricular sensed or paced event of the preceding heart cycle. Thus in an embodiment, an AEI runs from the atrial sensing unit sensing an electric event in the atrium or the atrial pulse generator generating an atrial stimulating pulse. In another embodiment, the AEI runs from ventricular sensing unit sensing an electric event in the ventricle or the ventricular pulse generator generating a ventricular stimulating pulse. Both these embodiments work equally well. It is though important that the IMD runs according to one of these embodiments regardless of the operation mode.

The controller controls the atrial sensing unit to sense for any atrial event during the time window of the first AEI in step S1. If an atrial event is sensed by the atrial sensing unit the operation continues to step S5. However, if no atrial event is sensed following expiry of the first AEI in step S3, the controller controls the atrial pulse generator 120 to generate an atrial stimulating pulse that is delivered to the atrium in step S4. This is schematically illustrated by A in the timing and waveform diagram of FIG. 6. P indicates the atrial depolarization that occurs following the paced or sensed atrial event. Generating an atrial stimulating pulse in step S4 or sensing an intrinsic atrial event step S2 starts a first AVI in step S5.

The controller controls the ventricular sensing unit to sense for any ventricular event during the time window of the first AVI in step S6, though not in the blanking period (BP) which immediately follows the delivery of the atrial stimulating pulse in step S4. If a ventricular event is sensed by the ventricular sensing unit the operation returns back to step S1 to start a new first AEI. In this case no mode switch is triggered and the IMD continues to operate in the first mode.

However, if no ventricular event is sensed following expiry of the first AVI in step S7, the controller controls the ventricular pulse generator 130 to generate a ventricular stimulating pulse that is delivered to the ventricle in step S8. This is schematically illustrated by V in the timing and waveform diagram of FIG. 6. R indicates ventricular depolarization that occurs following a ventricular sensed or paced event. In the latter case, evoked response has thus occurred. T represents the ventricular repolarization.

Following generation of the ventricular stimulating pulse in step S8, the controller triggers the evoked response detector to start sensing in step S9 for any evoked response of the ventricle in response to the delivered ventricular stimulating pulse. If the evoked response detector detects an evoked response the operation continues back to step S1, where a new first AEI is started and the operation of the IMD continues in the first mode.

However, if no evoked response is sensed by the evoked response detector following expiry of the defined evoked response time interval, the controller switches operation from the first mode to the second mode in step S10.

The reason for this temporary block of back-up pulses and mode switch will now be described with reference to FIG. 6. Assume that a PVC occurred during the blanking period (BP) following atrial pacing. BP is a short time interval after the delivery of the atrial stimulating pulse during which the ventricular sense amplifier is disabled and therefore cannot detect any signals. The reason for this BP is that the ventricular sensing unit otherwise could sense an atrial paced event and interpret it as an intrinsic ventricular event. Thus, since the ventricular sensing unit is temporary disabled during the BP it will not detect the PVC. If the delivered atrial stimulating pulse does not trigger any intrinsic ventricular event, the IMD will generate and deliver a ventricular stimulating pulse after expiry of the AVI. In this case there is a significant risk that the ventricular pulse will be delivered during the refractory period following the PVC. The refractory period, represented by the R wave in FIG. 6, is the period during which the heart will not response to any ventricular stimulation. No capture of the delivered ventricular stimulating pulse will consequently occur in this example. If the IMD would operate according to the prior art, a back-up pulse would be delivered and this back-up pulse can therefore coincident with the vulnerable period of the heart cycle or PVC, normally coincident with a part of the T-wave. Such back-up pacing in the vulnerable period is a high risk for triggering tachycardia and ventricular fibrillation.

The invention in clear contrast does not deliver the back-up pulse following the first detected failure of triggering evoked response. This means that the controller prevents the ventricular pulse generator from generating any back-up pulse in the first mode if the evoked response detector does not detect any evoked response to the delivered ventricular stimulating pulse.

Therefore in step S10 the controller switches operation from the first mode to the second mode and the method continues to step S11. In step S11 a second AEI is started. This second AEI can be equal to the first AEI used in the first mode but is preferably shorter than the first AEI, which is further described herein. The atrial sensing unit is configured to sense any intrinsic atrial events in step S12 during the second AEI and if such an atrial event is sensed the operation continues to step S15. However, if no atrial event is sensed at the expiry of the second AEI in step S13 the controller controls the atrial pulse generator to generate and deliver, through the switch and atrial lead, an atrial stimulating pulse to the atrium in step S14. The next step S15 starts a second AVI in response to the sensed atrial event in step S12 or the generation of the atrial stimulating pulse in step S14. The second AVI could be equal to the first AVI in the first mode or could be shorter than the first AVI, which is further described below.

The ventricular sensing unit monitors the ventricle for the purpose of detecting any intrinsic ventricular event following expiry of the ventricular blanking period in step S16. If such a ventricular event is sensed in step S16, the method continues to step S24 or optionally to a step S23 and then to step S24. In the optional step S23, an event detector 190 of the IMD 100, see FIG. 2, increments a first counter (counter A in FIG. 7) by one to indicate that a ventricular event is sensed by the ventricular sensing unit 135 when the IMD 100 is operating in the second mode.

If no ventricular event is sensed prior the end of the second AVI in step S17, the controller causes the ventricular pulse generator to generate a ventricular stimulating pulse that is delivered by the switch and the ventricular lead to the ventricle in step S18. The output energy of the ventricular stimulating pulse could be the same regardless of the operation mode of the IMD. In an alternative embodiment, the ventricular pulse generator generates a ventricular stimulating pulse with higher output energy when operating in the second mode as compared to a ventricular stimulating pulse generated when operating in the first mode. For instance, the amplitude of the ventricular stimulating pulse could about 1 to 2 times the amplitude used in the first mode.

The evoked response detector starts sensing, after a short period of time from the pulse delivery, for any evoked response in step S19. If the delivered ventricular stimulating pulse caused an evoked response as detected by the evoked response detector, the method continues to step S24, optionally through step S22. In step S22, the event processor increments a second counter (counter B in FIG. 7) by one in response to the detection of evoked response when the IMD is operating in the second mode.

If however the evoked response detector once more failed to detect any evoked response by the ventricle, the method continues to step S20, where a back-up pulse is generated by the ventricular pulse generator and delivered to the ventricle by the switch and the ventricular lead. The back-up pulse is preferably generated to have higher output energy than the ventricular stimulating pulse generated by the ventricular pulse generator in the first mode. For instance, if the ventricular pulse generator generates ventricular stimulating pulses with an amplitude of about 1.5 V in the first mode, the back-up pulse can have an amplitude between 4 and 5 V, e.g. 4.5 V. The above mentioned amplitude range is suitable regardless whether increased output energy is used for the ventricular stimulating pulses generated in the second mode.

The method continues to step S24 optionally through step S21. In step S21 the event processor increments a third counter (counter C in FIG. 7) by one if the evoked response detector failed to detect an evoked response to a delivered ventricular stimulating pulse when the IMD is operating in the second mode.

The controller switches operation from the second mode to the first mode in step S24 and the method returns back to step S1 to initiate a new heart cycle.

Thus, according to the invention, once the second mode is initiated the IMD operates in this mode at most during one heart cycle to switch back to the first mode either due to a sensed ventricular event, a detected evoked response or a delivered back-up pulse.

Furthermore, the temporary prevention of back-up pulse delivery in the first mode occurs at most during one heart cycle. Thus, even if the evoked response detector fails to detect an evoked response during two consecutive heart cycles, the back-up pulse is only prevent for the first heart cycle when the IMD is operating in the first mode. The mode is then switched, for the second heart cycle, to the second mode to allow delivery of a back-up pulse if no evoked response is detected also in this heart cycle.

The reason for this multi-mode operation and switch from the first mode to the second mode upon failure to detect evoked response is to verify that the failure of capture and evoked response is due to a PVC/undersensed intrinsic ventricular event or due to unsuitable settings of the IMD, in particular the sensing threshold used by the ventricular sensing unit and/or the output energy of the ventricular stimulating pulse from the ventricular pulse generator. The probability of having two PVCs or undersensed intrinsic ventricular events in two consecutive heart cycles that are further timed so that they will not be sensed in any of the heart cycles is very low and next to neglectable. Thus, if no evoked response is detected in the second mode in step S19, it is highly likely that the detection failure is rather due to IMD settings that are not optimal than multiple PVCs and a back-up pulse can therefore be safely delivered.

In an embodiment, the second AEI is shorter than the first AEI. This means that delivery of an atrial stimulating pulse in the second mode will occur at an interval that is significantly shorter than the ordinary time interval, i.e. the first AEI in the first mode. Reducing the cycle time through this reduction in the AEI in the second mode further reduces the risk of undersensing a PVC or intrinsic ventricular event in the blanking period since the probability for a new PVC or intrinsic ventricular event in the subsequent blanking period is remote especially when dislocating the timing of the subsequent blanking period as compared to the timing of the preceding blanking period by having different AEI lengths in the two modes. A possible interval for the second AEI could be about 0.5 to 0.9 times, preferably about 0.7 to 0.9 times the length of the first AEI employed in the first mode.

The second AVI employed in the second mode can also be shorter than the first AVI used in the first mode. The reason for this reduction in AVI would be to reduce the heart cycle length to thereby reduce the time from the failure to trigger ejection response and to the next ventricular stimulation in the second mode. For instance, if the failure to trigger ejection response is due to too low stimulation levels and no PVC occurred, it can be advantageous to reduce the time up to the next ventricular stimulation. A reduced AVI in the second mode could be from about 0.5 to 0.9 times the first AVI used in the first mode.

The IMD can in one embodiment operate with reduced AEI in the second mode as compared to the AEI used in the first mode. In another embodiment, the IMD operates with reduced AVI in the second mode as compared to the AVI in the first mode. A further alternative embodiment combines the usage of a reduced AEI and a reduced AVI in the second mode and then having normal or regular AEI and AVI in the first mode.

With reference to FIG. 2, the counters that are preferably managed by the event processor 190 based on the different outcomes in the second mode are of high diagnostic value and are therefore preferably stored in the memory 180. The values of the counters can be uploaded to the programmer by the transceiver 170 upon request by the programmer. The uploaded values can then be analyzed by the physician to determine the patient status, such as diagnosed as having frequent PVCs, and/or the status of the IMD, such as improper IMD settings. In the latter case, the physician can determine updated settings and generate, through the programmer, reprogramming commands that are transmitted to the IMD 100 and received by the transceiver 170. The commands are forwarded to the controller 140 to thereby cause a reprogramming of the relevant settings.

In a particular embodiment, the event processor 190 not only increments the respective counters but also logs time information at which a particular counter is incremented. This time information provides further diagnostic value to the physician to thereby perhaps detect trends when different cardiac events represented by the counters are occurring.

The counters managed by the event processor 190 can also be used by the IMD 100 itself for controlling its operation. For instance, if the third counter is significantly larger than the first and second counter and in particular the second counter, this could be an indication that the sensing threshold employed by the ventricular sensing unit could be set too high to thereby miss detection of capture and evoked response following ventricular stimulation. The controller 140 can then trigger a threshold search based on the counter values and in particular when the third counter exceeds a threshold value or the quotient of the third and second counter exceeds a threshold value. Threshold searching is well known in the art and is not further described herein.

Alternatively, or in addition, if the third counter or the quotient between the third and second counter exceeds a defined threshold value, it can be an indication that the output energy of the ventricular stimulating pulse is too low to trigger capture. The controller 140 then controls the ventricular pulse generator 130 to increase the output energy of the ventricular stimulating pulses that are delivered in preferably both the first and second mode. Optionally, the controller 140 can triggers a search for suitable pulse energy level to thereby find a pulse energy level that is sufficient to trigger capture but is not unnecessarily large to thereby drain too much power from the battery 160.

A further IMD-triggered adjustment of its settings based on the counters could be to adjust the AEI and/or AVI, preferably by shortening the time interval slightly in the first mode and in the second mode. The controller 140 can thereby be configured to automatically decrease the AEI and/or AVI with a defined reduction value or trigger a search for optimal AEI/AVI, which is well known in the art, if any of the counters, preferably the third counter or quotient between the third and second counter exceeds a threshold value.

The threshold value(s) used by the IMD 100 in these comparison embodiments is(are) stored in the memory 180. The threshold value(s) is(are) preferably programmable and can be set by the physician by transmitting a reprogramming command to the transceiver 170 by means of the programmer. Suitable threshold values are preferably patient specific and determined in a non-inventive manner by the physician.

In yet another embodiment, IMD 100 can operate according to a third mode. This third mode preferably corresponds to the traditional Autocapture mode. Thus, in the third mode the controller 140 is configured to control the atrial pulse generator to generate an atrial stimulating pulse following expiry of the first AEI, i.e. the same AEI interval that is employed in the first mode. Additionally, the controller 140 controls the ventricular pulse generator 130 to generate a back-up pulse that is delivered to the ventricle by the ventricular lead if the evoked response detector does not detect an evoked response to a delivered ventricular stimulating pulse.

The switch from the first or second mode to the third mode is preferably based, in this embodiment, on any of the counters managed by the event processor 130. Thus, if any of the counters exceeds a respective associated thresholds value the controller 140 triggers a switch to the third mode. The reason for this bypassing of the first and second modes could be that a counter exceeding its threshold value could well indicate inappropriate settings and thereby inappropriate switches from the first mode to the second mode. It could therefore be preferred to at least temporarily stop the operations in the first and second mode to allow the physician to reprogram the settings at a next patient follow up occasion. For instance, the AVI, blanking periods, etc. could be reprogrammed to better adapt to the particular patient and thereby prevent unnecessary switches between the first and second modes.

In yet another embodiment the above mentioned third mode is the normal, default mode of the IMD 100. This means that the IMD 100 is programmed to start operation according to the third mode to thereby always deliver back-up pulses if a delivered ventricular stimulating pulse fails to evoke a response in the ventricle. In such a case, the IMD 100 preferably comprises a PVC detector 150 that is configured to detect the occurrence of PVCs in the ventricles. PVC detectors in IMDs are per se well documented in the art and can, for instance, perform the PVC detection by analyzing the intracardiac electrogram signals acquired by the data acquisition system 155 or detecting the PVC as a ventricular event sensed by the ventricular sensing unit 135 without a preceding sensed or paced atrial event. Such event-based sensing of PVCs will, though, of course not detect any PVCs occurring during the blanking periods as previously mentioned.

The PVC detector 150 preferably also counts the number of such detected PVCs and preferably the timing of the PVCs. This information can be stored in the memory 180 and can be uploaded to the programmer by the transceiver 170 and used for diagnostic purposes. Additionally, or alternatively, the controller 140 could be configured to switch from the third mode to the first mode if the number of detected PVCs within a defined time interval exceeds a threshold number. The threshold value is preferably determined by the physician for the particular patient and can be programmed into the IMD 100 by the programmer. In such a case, the patient has an increased risk of having PVCs and thereby a risk of having a PVC occurring during the blanking period following atrial pacing, which may cause pacing-triggered tachycardia or ventricular fibrillation as previously described. The IMD 100 should therefore instead operate according to the first mode and temporarily switch to the second mode when necessary in order to reduce the risk of inducing tachycardia and ventricular fibrillation.

Embodiments as disclosed herein relates to a modified form of Autocapture that is safe also for patients prone to PVCs or episodes with true undersensing.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

What is claimed is:

1. A cardiac stimulating method comprising:
   providing a lead connector connectable to an atrial lead having at least one electrode and a ventricular lead having at least one electrode;
   connecting an atrial pulse generator to the lead connector and configuring the atrial pulse generator to generate atrial stimulating pulses;
   connecting an atrial sensing unit to the lead connector and configuring the atrial sensing unit to sense electric events in an atrium of a heart;
   connecting a ventricular pulse generator to the lead connector and configuring the ventricular pulse generator to generate ventricular stimulating pulses;
   connecting a ventricular sensing unit to the lead connector and configuring the ventricular sensing unit to sense electric events in a ventricle of the heart, the ventricular sensing unit comprising an evoked response detector configured to detect an evoked response of the ventricle to a ventricular stimulating pulse generated by the ventricular pulse generator and delivered to the ventricle by the ventricular lead;
   connecting a controller to the atrial pulse generator, the atrial sensing unit, the ventricular pulse generator and the ventricular sensing unit and configuring the controller to control operation of the ventricular pulse generator according to a first mode or a second mode and configuring the controller to trigger a switch from the first mode to the second mode based on the evoked response detector failing to detect an evoked response to a delivered ventricular stimulating pulse;
   wherein in the first mode the controller is configured to prevent the ventricular pulse generator from generating a back-up if the evoked response detector does not detect an evoked response to a delivered ventricular stimulating pulse; and
   wherein in the second mode the controller is configured to control the ventricular pulse generator to generate a back-up pulse delivered to the ventricle by the ventricular lead if the evoked response detector does not detect an evoked response to a delivered ventricular stimulating pulse; and
   configuring a premature ventricular contraction detector to detect premature ventricular contractions in the ventricle, wherein the controller is configured to switch from a third mode to the first mode based on the premature ventricular contraction detector detecting a number of premature ventricular contractions during a defined time interval exceeding a threshold number, wherein in the third mode the controller is configured to control the atrial pulse generator to generate an atrial stimulating pulse following expiry of the first atrial escape interval and control the ventricular pulse generator to generate a back-up pulse delivered to the ventricle by the ventricular lead if the evoked response detector does not detect an evoked response to a delivered ventricular stimulating pulse.

2. The method according to claim 1, wherein the controller is configured to trigger a switch from the second mode to the first mode based on i) the ventricular sensing unit sensing an electric event in the ventricle in the second mode, ii) the evoked response detector detecting an evoked response to a delivered ventricular stimulating pulse in the second mode, or iii) the ventricular pulse generator generating the back-up pulse in the second mode.

3. The method according to claim 1, wherein the controller is configured to control operation of the atrial pulse generator and the ventricular pulse generator according to the first mode or the second mode, wherein in the first mode the controller is configured to control the atrial pulse generator to generate an atrial stimulating pulse following expiry of a first atrial escape interval, and wherein in the second mode the controller is configured to control the atrial pulse generator to generate an atrial stimulating pulse following expiry of a second atrial escape interval, the second atrial escape interval being shorter than the first atrial escape interval.

4. The method according to claim 1, wherein in the first mode the controller is configured to control the atrial pulse generator to generate the atrial stimulating pulse following expiry of the first atrial escape interval from the atrial sensing unit sensing an electric event in the atrium or the atrial pulse generator generating an atrial stimulating pulse and in the second mode the controller is configured to control the atrial pulse generator to generate the atrial stimulating pulse following expiry of the second atrial escape interval from the atrial sensing unit sensing the electric event in the atrium or the atrial pulse generator generating the atrial stimulating pulse.

5. The method according to claim 1, wherein in the first mode the controller is configured to control the atrial pulse generator to generate the atrial stimulating pulse following expiry of the first atrial escape interval from the ventricular sensing unit sensing an electric event in the ventricle or the ventricular pulse generator generating a ventricular stimulating pulse and in the second mode the controller is configured to control the atrial pulse generator to generate the atrial stimulating pulse following expiry of the second atrial escape interval from the ventricular sensing unit sensing the electric event in the ventricle or the ventricular pulse generator generating the ventricular stimulating pulse.

6. The method according to claim 1, wherein in the first mode the controller is configured to control the ventricular pulse generator to generate a ventricular stimulating pulse following expiry of a first atrioventricular interval from the atrial sensing unit sensing an electric event in the atrium or the atrial pulse generator generating an atrial stimulating pulse and wherein in the second mode the controller is configured to control the ventricular pulse generator to generate a ventricular stimulating pulse following expiry of a second atrioventricular interval from the atrial sensing unit sensing the electric event in the atrium or the atrial pulse generator generating the atrial stimulating pulse, the second atrioventricular interval being shorter than the first atrioventricular interval.

7. The method according to claim 1, wherein in the second mode the controller is configured to control the ventricular pulse generator to generate the ventricular pacing pulse at a higher output energy as compared to a ventricular pacing pulse generated by the ventricular pulse generator in the first mode.

8. The device according to claim 1, further comprising an event processor operable in the second mode and configured to increment a first event counter based on the ventricular sensing unit sensing an electric event in the ventricle in the second mode, increment a second event counter based on the evoked response detector detecting an evoked response to a delivered ventricular stimulating pulse in the second mode, and increment a third event counter based on the ventricular pulse generator generating the back-up pulse in the second mode.

9. A cardiac stimulating method comprising:
   starting a first atrial escape interval;
   delivering an atrial stimulating pulse to an atrium of a heart if no electric event of the atrium is detected before expiry of the first atrial escape interval;
   starting a first atrioventricular interval based on detection of the electric event of the atrium prior expiry of the first atrial escape interval or based on delivery of the atrial stimulating pulse following expiry of the first atrial escape interval;
   delivering a ventricular stimulating pulse to a ventricle of the heart following expiry of the first atrioventricular interval if no electric event of the ventricle is detected before expiry of the first atrioventricular interval;
   monitoring an evoked response of the ventricle to the ventricular stimulating pulse delivered following expiry of the first atrioventricular interval;
   starting a second atrial escape interval if no evoked response of the ventricle to the ventricular stimulating pulse delivered following expiry of the first atrioventricular interval is detected, the second atrial escape interval being equal to or shorter than the first atrial escape interval;
   delivering an atrial stimulating pulse to said atrium if no electric event of the atrium is detected before expiry of the second atrial escape interval;
   starting a second atrioventricular interval based on detection of the electric event of the atrium prior expiry of the second atrial escape interval or based on delivery of the atrial stimulating pulse following expiry of the second atrial escape interval, the second atrioventricular interval being equal to or shorter than the first atrioventricular interval;
   delivering a ventricular stimulating pulse to the ventricle following expiry of the second atrioventricular interval if no electric event of the ventricle is detected before expiry of the second atrioventricular interval;
   monitoring an evoked response of the ventricle to the ventricular stimulating pulse delivered following expiry of the second atrioventricular interval; and
   delivering a back-up pulse to the ventricle if no evoked response of the ventricle to the ventricular stimulating pulse delivered following expiry of the second atrioventricular interval is detected.

* * * * *